United States Patent [19]
Kulle et al.

[11] Patent Number: 4,874,369
[45] Date of Patent: Oct. 17, 1989

[54] SELF-PRIMING INJECTION SITE WITH CHECK VALVE

[75] Inventors: Lee Kulle, Mundelein; Vince Desecki, Ingleside; John M Hess, III, Cary, all of Ill.

[73] Assignee: Baxter International Inc., Deerfield, Ill.

[21] Appl. No.: 78,485

[22] Filed: Jul. 27, 1987

[51] Int. Cl.$^4$ .......................................... A61M 37/00
[52] U.S. Cl. ..................................................... 604/86
[58] Field of Search ................ 604/86, 167, 280, 283, 604/403, 415; 215/247

[56] References Cited

U.S. PATENT DOCUMENTS

| | | |
|---|---|---|
| 3,572,375 | 3/1971 | Rosenberg . |
| 3,650,093 | 3/1972 | Rosenberg . |
| 3,710,942 | 1/1973 | Rosenberg . |
| 4,000,739 | 1/1977 | Stevens . |
| 4,000,740 | 1/1977 | Mittleman . |
| 4,048,996 | 9/1977 | Mittleman et al. . |
| 4,133,441 | 1/1979 | Mittleman et al. . |
| 4,294,249 | 10/1981 | Sheehan et al. . |
| 4,338,934 | 7/1982 | Spademan . |
| 4,405,316 | 9/1983 | Mittleman . |
| 4,424,833 | 1/1984 | Spector et al. . |
| 4,566,493 | 1/1986 | Edwards et al. . |
| 4,610,674 | 9/1986 | Suzuki et al. . |

FOREIGN PATENT DOCUMENTS

| | | |
|---|---|---|
| 0109903 | 5/1984 | European Pat. Off. . |
| 2004771 | 11/1969 | France . |
| 2033230 | 5/1980 | United Kingdom . |

*Primary Examiner*—John D. Yasko
*Attorney, Agent, or Firm*—Mary J. Schnurr; Amy L. H. Rockwell; Paul C. Flattery

[57] ABSTRACT

A self-priming injection site having a stopper that resists dislocation or removal from the injection site. The stopper is positioned within the plastic housing between a top with an open center and an intermediate ledge having an upturned lip. The stopper includes an annular groove that receives the upturned lip of the intermediate ledge, to assist in holding the stopper in compression within the housing. An arm portion allows the intravenous fluid to enter the injection site on a path approximately parallel to and immediately adjacent to the ledge and the bottom of the stopper. A check valve may be positioned within the arm portion.

27 Claims, 4 Drawing Sheets

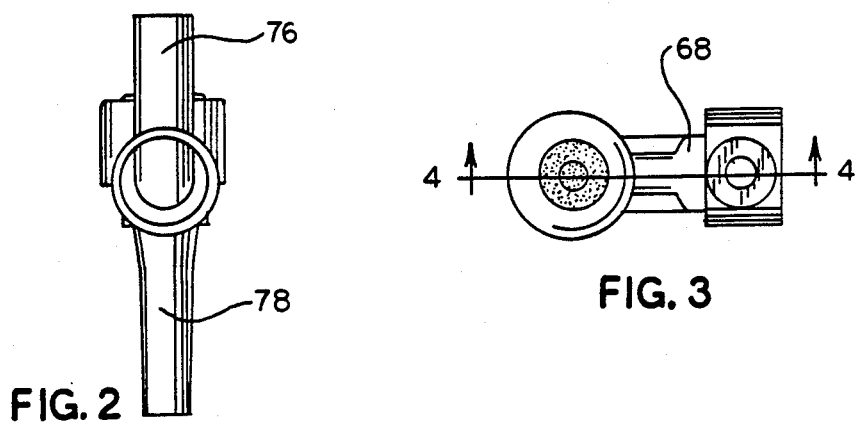
FIG. 2
FIG. 3
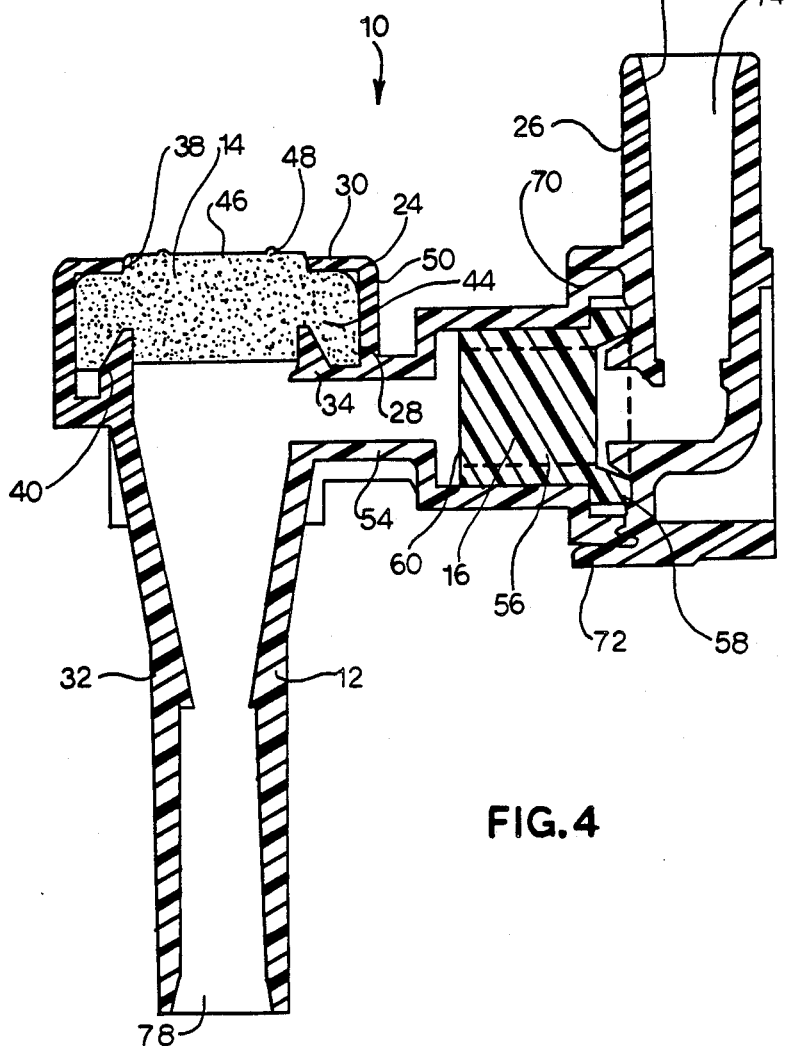
FIG. 4

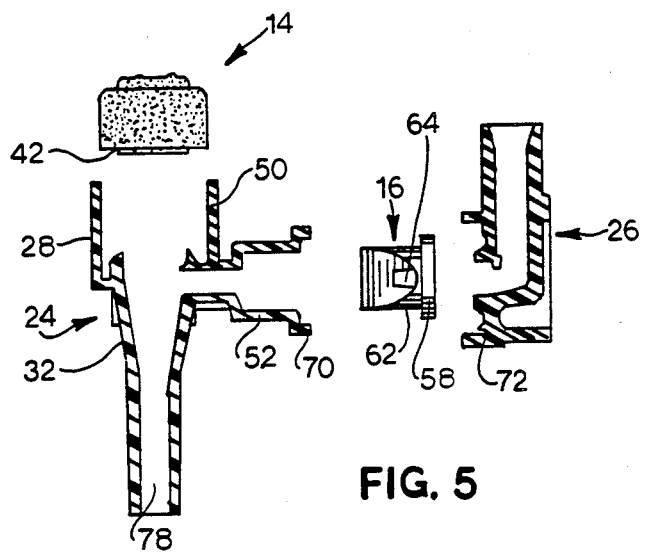
FIG. 5
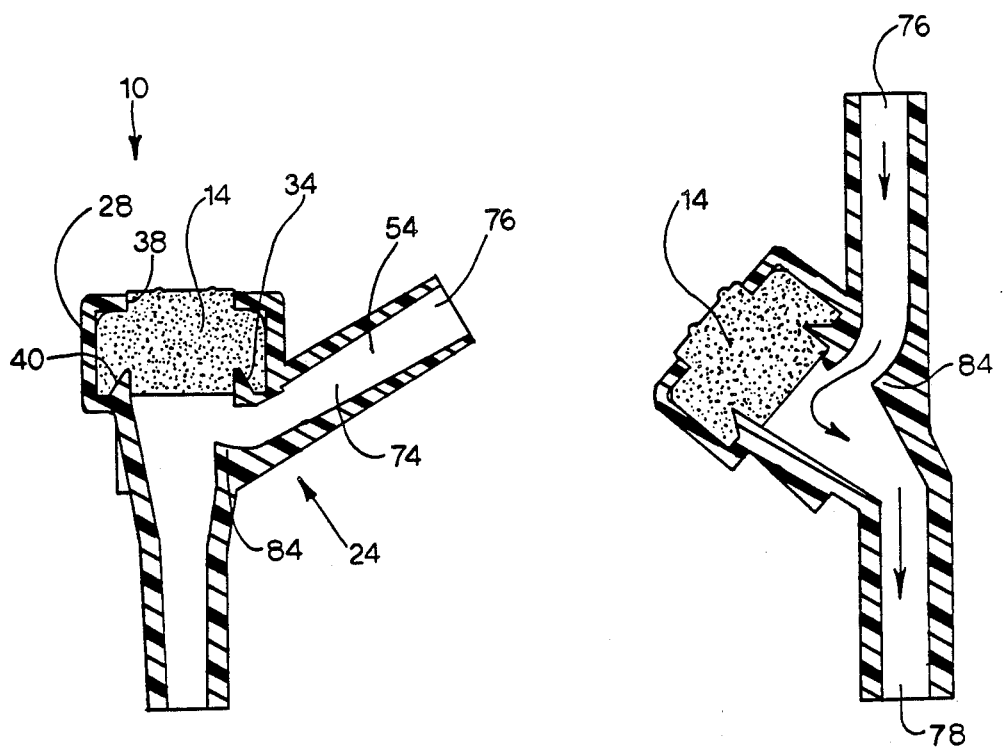
FIG. 6
FIG. 7

SELF-PRIMING INJECTION SITE WITH CHECK VALVE

BACKGROUND OF THE INVENTION

This invention relates to a self-priming injection site. More particularly, this invention relates to a combination injection site and check valve for use in a parenteral solution administration apparatus whereby the apparatus is constructed so that the fluid flowing through the check valve automatically primes the injection site.

Presently, injection sites are generally 'Y' shaped with one of the top arms of the 'Y' being covered by a sleeve stopper formed of a latex compound. The sleeve stopper known in the prior art surrounds both the inside and the outside of the upper portion of the hollow arm. The sleeve stopper has a center that extends across the hollow arm of the injection site to prevent contaminants from entering the intravenous administration set. The closed center surface is generally located adjacent to the end of the hollow arm. To add medication or other solutions to the fluids already passing through the administration set, medical personnel use a syringe or other injection apparatus to pierce through the center surface of the sleeve stopper. Upon the needle being inserted into and removed from the sleeve stopper, the sleeve stopper may be damaged, rearranged, or even removed from the injection site. The sleeve-type stopper is particularly susceptible to being pulled from the injection site by large gauge needles since the sleeve-type stopper depends solely on the friction between itself and the arm of the injection site to retain the stopper in proper position. Since the friction alone is often insufficient, a vinyl heat seal band may be placed around the outside of the sleeve stopper and the adjacent portion of the arm. Although the heat seal band has improved the retention of the stopper in the arm, the results have still not been totally satisfactory.

The stoppers are generally formed of latex or a similar material that substantially reseals upon the needle being removed. However, repeated piercings damage the stopper, especially piercings done in such a manner that they create substantially larger openings. Once the stopper has been damaged by piercing, the stopper develops an even greater propensity to being moved from its proper position.

The removal of the stopper from the injection site causes an assortment of problems including fluids leaking from the administration set and the introduction of contaminants and air into the intravenous solution. The problem of stoppers that do not remain in their proper position on the injection site is particularly troublesome since the injection site is not independently removable from the administration set. The entire administration set must be changed to allow a new injection site to be put into place. It would be an advantage to provide an injection site which can withstand a large number of needle piercings and removals even when subjected to high pressures often associated with injections from small syringes, which may exceed 125 p.s.i.

It is an object of this invention to provide an improved injection site which can withstand a number of needle piercings and removals without the stopper being repositioned or removed from the injection site.

It is a further object of this invention to provide an injection site that is self-priming or easily primed.

One additional object of this invention is to provide minimal amounts of internal residual volume within the injection site lumen.

SUMMARY OF THE INVENTION

The foregoing advantages are accomplished and the shortcomings of the prior art are overcome by the present self-priming injection site which is comprised of a housing including a cylindrical portion having a top with a center opening, an 'O'-shaped ledge having an upturned lip, and a cone-shaped outlet portion. A disc-shaped stopper is positioned between the top and the ledge. The bottom surface of the stopper is provided with an annular groove that receives the ledge upturned lip. An arm portion of the housing joins the cylindrical housing just below the ledge. A valve is positioned within the arm portion and/or within a valve housing which is joined to the end of the arm portion. The intake of the valve housing and the outlet of the cone-shaped portion are approximately parallel to one another. Thus, intravenous tubing, attached to the inlet and outlet, will hang in an approximately vertical direction. In a first embodiment of the invention, the arm portion is approximately perpendicular to the cylindrical housing. Since the valve outlet is immediately below the housing ledge, fluid flows through the valve into the area immediately adjacent to the stopper, forcing the air out of the housing. Thus, the injection site is substantially self-priming.

BRIEF DESCRIPTION OF THE DRAWINGS

FIG. 2 is a side view of the injection site of FIG. 1.

FIG. 3 is a top view of the injection site of FIG. 1.

FIG. 4 is cross-sectional view of the injection site of FIG. 1 taken along the lines 4—4 of FIG. 3.

FIG. 5 is an exploded view of the injection site of FIG. 1.

FIG. 6 is a second embodiment of the injection site that is the subject of the instant invention.

FIG. 7 is a third embodiment of the injection site that is the subject of the instant injection.

DETAILED DESCRIPTION OF THE INVENTION

Figure 1:
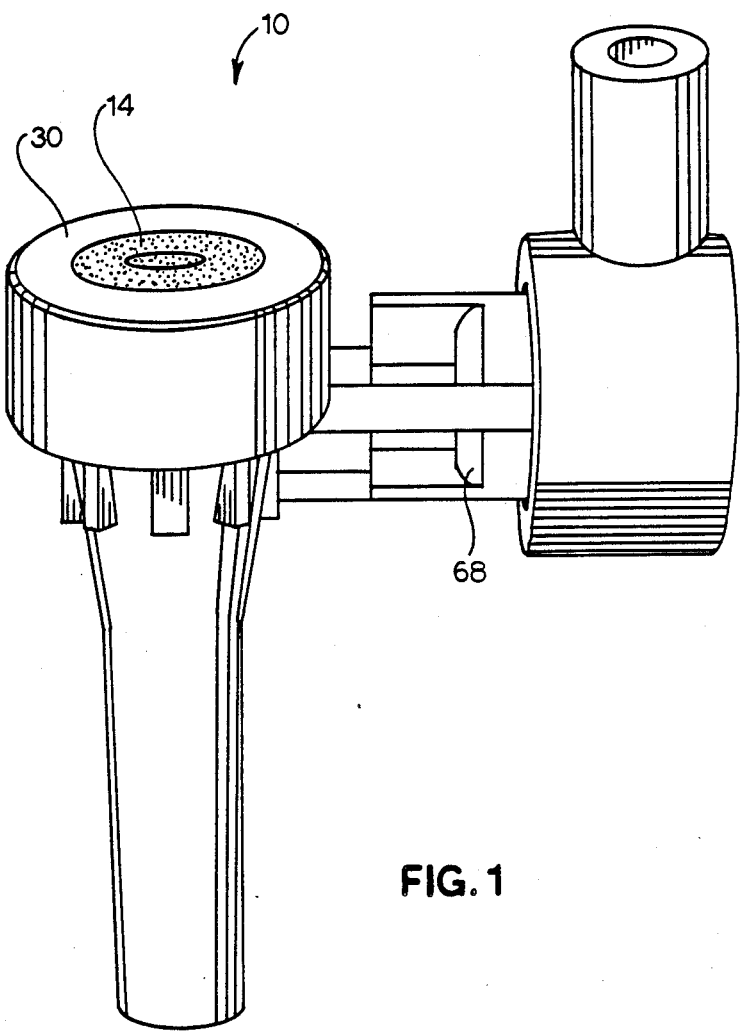
FIG. 1 is a perspective view of an injection site that is a first embodiment of the subject invention.
Figure 8:
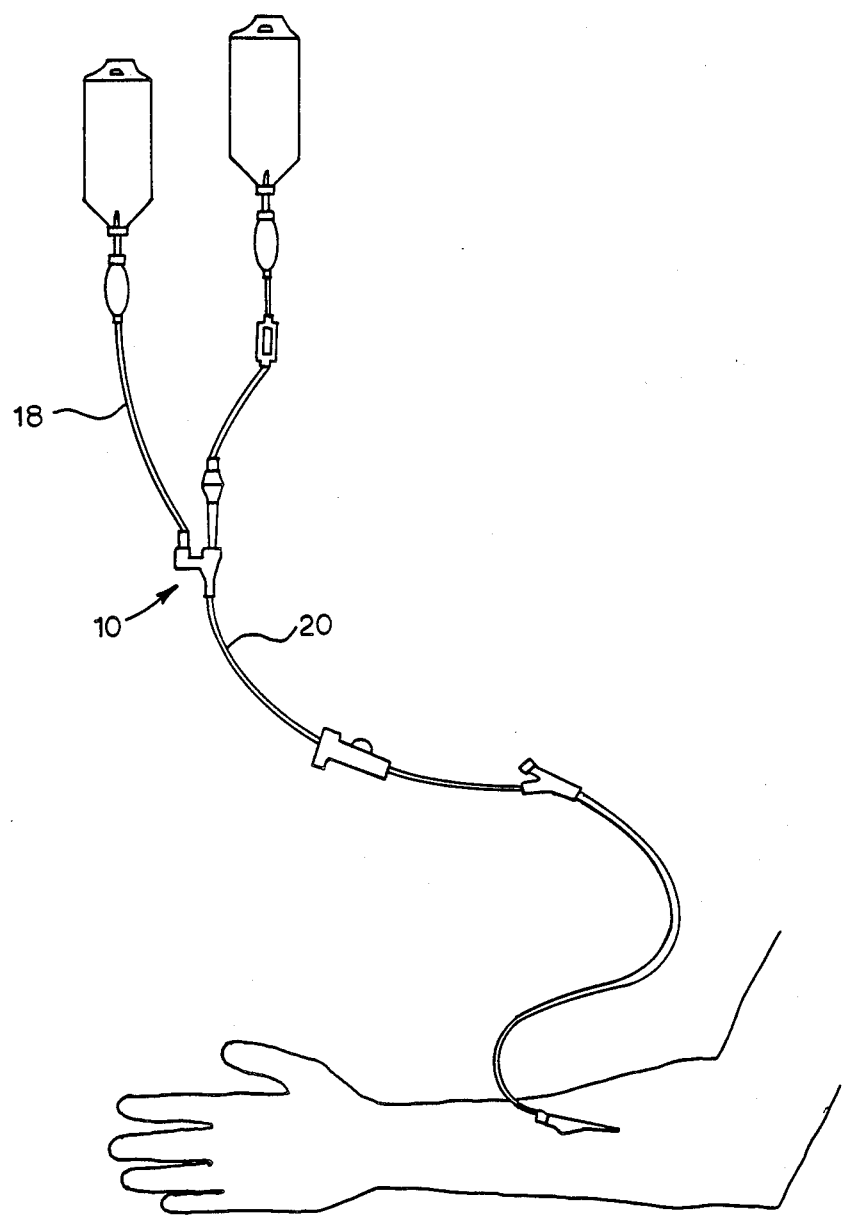
FIG. 8 is a perspective view of a parenteral administration set utilizing the injection site of FIG. 1.

The injection site of the instant invention can be seen by reference to the figures. In general, the injection site, indicated generally as 10, includes a housing, a stopper 14, and a valve 16. As shown in FIG. 8, the injection site 10 is connected between tubing 18 and tubing 20 in an apparatus for administering a parenteral solution to a patient.

Generally, the injection site constitutes a portion of the passageway of the intravenous fluid continually administered to the patient. As the patient's therapy requires supplemental intravenous medication or other intermittant administration of a second fluid, a syringe or other injection apparatus is used to insert medication into the intravenous fluid. The needle is inserted and then withdrawn through stopper 14. Since the intravenous solution may be administered to the patient for lengthy periods of time, it is desirable to have a stopper that can withstand numerous piercings and removals of the needle, even under high pressure.

Housing 12 may be a combination housing of a stopper housing 24 and valve housing or second housing 26, as shown in FIG. 4, or may be a single housing as shown in FIG. 6. The stopper housing or stopper portion 24 includes an approximately cylindrical portion 28, a top 30, an intermediate ledge 34, and a cone-shaped outlet portion 32. Cone-shaped outlet portion 32 helps deflect a needle into the center of the injection site to prevent the needle from piercing the sidewall of the injection site.

Top 30 has an open center 38, while the ledge 34, which extends the entire 360° around the circumference of cylindrical portion 28, has an upwardly turned lip 40. The stopper 14 is approximately disc-shaped with its bottom surface having an annular groove 42 that receives ledge lip 40. Top 30 and ledge 34 hold stopper 14 in vertical and/or diametric compression to securely retain the stopper within the housing 12. Groove 42 creates an ear 44 around the circumference of the stopper 14. At least one dimension of the ear 44, such as the height, must be larger than the distance from the lip 40 to the top 30 to deter the repositioning or removal of the stopper when the needle is inserted and removed therefrom.

Because the stopper is held in compression, its center 46 extends through the open center 38 of the housing. Raised center 46 facilitates the sterilization of the stopper, by providing easier accessibility for wiping with an anti-microbial agent, such as isopropyl alcohol, with abrasive action. Prior art injection sites having a stopper that is recessed below the remainder of the top of the injection site allow the anti-microbial agent to accumulate in a puddle on the top of the stopper. Particulate matter may also collect on the top of the stopper, and may be transmitted inside the injection site to the I.V. solution when a needle pierces the stopper. The raised or flush stopper design of the instant invention permits a clean drain of the anti microbial agent from the stopper, as well as facilitating the cleaning of the stopper.

Raised center 46 has an embossed ring 48 that defines the preferred target area for insertion of the needle. A needle inserted within the embossed ring 48 exerts a force that is small enough that it generally does not reposition or remove the stopper from the housing. The target area is at least 0.15 inches in diameter, large enough to accept large bore needles, such as 16 or 18 gauge needles, and multiple simultaneous needles.

The stopper housing 24 is molded as one unit. Immediately after molding, the top 30 of the housing is a vertical extension of the sides 50 of the cylindrical portion 28, as shown in FIG. 5. After the stopper 14 is positioned on the ledge 34, the top edge of the cylinder sides 50 is bent inwards to form the top 30 either by ultrasonic deformation, by heating or by cold forming. The unitary molded housing holding stopper 14 in compression provides for lower cost, easier assembly and more stable assembly dimensions. Because the dimensions are more precise, the performance of the injection site is more reliable.

The stopper housing 24 has an arm portion 54 joined to the cone-shaped outlet portion 32 immediately below ledge 34. Arm portion 54 provides for the main flow of fluid through the injection site. In the embodiment of the invention shown in FIGS. 1-5, the arm portion includes an enlarged section 54 that houses the valve 16. The valve in the embodiment shown is a duckbill type as will be described briefly herein and is described in more detail in U.S. Pat. No. 4,566,493. A variety of other valves may also be used. A valve housing portion 26 is joined to the stopper housing 24 by one of a variety of methods. Adhesive may be applied between the two parts or ultrasonic welding may be used to cause the two parts to merge together.

Valve 16 includes sides 56 extending to an annular collar 58. Valve sides 56 are positioned at an angle to form a slit 60 through which the fluid passes. The sides 56 are connected to one another through curved walls 62. Valve 16 also has tabs 64 positioned on the sides 56 adjacent the annular collar 58. The end of the valve at slit 60 is positioned very close to cone shaped outlet portion 32 of the housing, approximately 0.272 inches from the end of the valve to the outlet passageway in the embodiment described herein.

By combining the injection site and the check valve instead of positioning the check valve upstream from the injection site a number of advantages are achieved. The close proximity of the two components prevents any retrograde flow up the I.V. tubing. This is important for drugs that require minimum diluent or that must be administered quickly to the patient. In particular, vicous highly dense drugs that flow up the I.V. tubing require considerable time and fluid for purging the drug out of the tubing. The present design also minimizes the stagnant area where drugs can collect, to reduce the portion of the drug that is not administered to the patient.

Enlarged section 52 of the housing includes a flange 70 that surrounds and mates with the annular collar 58 of valve 16, while valve tabs 64 are received in notches 68 of the arm portion 54 of the housing. This arrangement helps to ensure that valve 16 does not twist within the housing. Since the clearance between valve sides 56 and sides 66 of the housing arm protion is very small, any twisting of valve 16 within the housing would disturb the proper operation of the valve.

Valve housing 26 includes a sleeve 72 that surrounds the flange 70 of the housing arm portion. Passageway 74 of valve housing portion 26 includes an approximately right angle turn. Fluid through the valve flows vertically downward through passageway 74, then horizontally through arm portion 54, then downward again through cone-shaped outlet 32. Thus, the tubing attached to the valve housing and to the outlet of the stopper housing 24 are approximately parallel to one another. Since this tubing generally hangs vertically, stopper 14 will generally be positioned on the top of the injection site where it is easily accessible to medical personnel, as shown in the figures. The vertical inlet of valve housing 26 has its outer edge positioned at least 0.75 inches from the center of stopper 14. This allows for easy access with the large bore needles and multiple simultaneous needles, as discussed above.

As the intravenous solution enters the valve housing 26, it makes an approximately right angle turn as shown in the embodiment of FIGS. 1-5, moves through the valve and directly across the bottom of the housing ledge 34 and across the bottom of the stopper 14. The fluid flow forces substantially all air within the stopper housing towards the outlet 78. The injection site is thus self-priming. In the prior art injection sites utilizing the sleeve stopper, the cavity located within the center of the sleeve stopper prevented a self-priming feature. Using the sleeve stopper, even a stream of liquid directed across the bottom of the rubber part could not force out the air located within the cavity. Air was removed by inverting the injection site while manually tapping on the housing.

The second and third embodiments of the invention, shown in FIGS. 6 and 7, respectively, also direct the fluid across the bottom of the stopper 14. The arm portion 54 of the embodiment shown in FIG. 6 joins the cylindrical portion 28 of the housing at an angle other than 90°. The intravenous solution enters the inlet 76 of the stopper housing 24 and flows down the passageway 74 of the arm portion. At the end of the arm portion is a ramp 84 which adjusts the direction of flow of the intravenous fluid to be approximately parallel to the bottom of the ledge 34 and the bottom of the stopper 14. This arrangement produces a self-priming injection site.

The stopper housing 24 that is shown in FIG. 6 may be molded of one piece since each opening in the housing forms a straight line from outside the housing to the center of the housing. The angle between the arm portion 54 and the cylindrical portion 28 was chosen as an angle other than 90° to utilize the benefit of a molded one-piece housing while creating an arrangement in which the injection site 10 hangs from vertical tubing in a manner so that the stopper 14 is generally on the top of the injection site. The angle between arm portion 54 and cylindrical portion 28 may be either greater or less than 90°.

The third embodiment shown in FIG. 7 is similar to that shown in FIG. 6. The inlet 76 of the injection site is vertical and parallel to the outlet 78. The third embodiment has a housing arm portion that forms with inlet 74 an angle greater than 90°, so that the housing may be molded from one piece. The embodiment shown in FIG. 7 is also one which has a self-priming or easy-priming feature. The device shown in FIG. 7 also utilizes a ramp 84 to modify the direction of the intravenous fluid so that it runs approximately parallel to and immediately adjacent to the bottom of the stopper 14. Again, the injection site hangs from vertical tubing in a manner such that the stopper 14 is generally on the top of the injection site.

It will thus be seen that through the present invention there is now provided a self-priming injection site which is simple in construction. The injection site also has the advantage of being capable of accepting many needle insertions and withdrawals without leaking or otherwise functioning improperly. The vertical and/or diametric compression of stopper 14, as well as the thickness of the latex stopper enhance the resalability of stopper 14.

While the invention has particularly been shown and described with reference to a number of preferred embodiments, it will be understood by those skilled in the art that variations in form, construction, and arrangement may be made therein without departing from the spirit and scope of the invention. All such variations are intended to be covered in the intended claims.

We claim:

1. An injection site for use in an apparatus for administering a parenteral solution to a patient, said injection site comprising:
    a stopper housing including a top with a center opening, a cylindrical portion having an O-shaped ledge positioned therein, said O-shaped ledge having a lip turn towards said top, and a cone-shaped outlet portion integral with the cylindrical portion and extending away from the top; and
    a disc-shaped stopper positioned in said center opening between the top and the ledge of the cylindrical portion.

2. An injection site as claimed in claim 1 wherein said stopper includes a bottom surface with an annular groove for receiving the lip of the O-shaped ledge.

3. An injection site as claimed in claim 2 wherein said stopper groove delineates an ear around the circumference of said stopper, a dimension of said ear being greater than the distance between said housing top and said ledge lip.

4. An injection site as claimed in claim 3, said injection site being adapted for the insertion of a needle, wherein a portion of said stopper protrudes from said center opening including a target location indicating the desired location for the insertion of the needle.

5. An injection site as claimed in claim 4 wherein the target location of said stopper is large enough to accept two needles.

6. An injection site as claimed in claim 4, the target location of said stopper being at least 0.15 inches in diameter.

7. An injection site as claimed in claim 3 wherein the bottom of said stopper forms a substantially flat coextensive surface with said ledge when the groove receives the ledge lip.

8. An injection site as claimed in claim 7 additionally comprising a valve with an outlet producing an output into said stopper housing below said ledge.

9. An injection site as claimed in claim 8 wherein said valve output is approximately parallel to and immediately adjacent to said coextensive surface.

10. An injection site as claimed in claim 8 wherein said valve outlet is directly connected to said housing.

11. An injection site as claimed in claim 8 wherein said valve has an input that is approximately parallel to the output of said housing.

12. An injection site as claimed in claim 8 wherein said stopper and said valve are enclosed in a common housing including said stopper housing and a valve housing, each comprising a single molded unit.

13. An injection site as claimed in claim 11 wherein said stopper and said valve are enclosed in a common housing including said stopper housing and a valve housing, each comprising a single molded unit.

14. An injection site as claimed in claim 3 wherein said stopper is in compression within said stopper housing.

15. An injection site for use in an apparatus for administering a parenteral solution to a patient, said injection site comprising:
    a unitary molded housing comprising a stopper portion and arm portion, said stopper portion including a cylindrical portion having a top with a center opening and a cone-shaped outlet portion, said cylindrical portion having positioned therein an 360° O-shaped ledge with a lip turned towards said top, said arm portion having an input and an output, said arm portion output being connected to said cylindrical portion immediately adjacent said ledge;
    a stopper being in compression within said housing, said stopper being substantially positioned between said top and said ledge, said stopper has a top surface and a bottom surface, the bottom surface having an annular groove receiving the lip of the O-shaped ledge, the bottom surface, forming a substantially coextensive surface with said ledge, the top surface protruding from said housing top; and
a valve positioned within said arm portion;
said housing arm portion accepting fluids at its input and releasing the fluids from its output across said coextensive surface to provide a substantially self-priming injection site.

16. An injection site as claimed in claim 15 additionally comprising a second housing being of a unitary molded construction, said second housing being connected to said stopper housing, adjacent said valve.

17. An injection site as claimed in claim 15 wherein said second housing includes an input that is approximately parallel to said cone-shaped outlet portion.

18. An injection site as claimed in claim 17 wherein said stopper groove delineates an ear around the circumference of said stopper, the height of said ear being greater than the distance between said top and said ledge lip.

19. An injection site as claimed in claim 18, said injection site being adapted for the insertion of a needle, wherein the portion of said stopper protruding from said center opening including a target location indicating the desired location for the insertion of the needle.

20. An injection site as claimed in claim 19 wherein the target location of said stopper is large enough to accept two needles.

21. An injection site as claimed in claim 20, the target location of said stopper being at least 0.15 inches in diameter.

22. An injection site as claimed in claim 15 wherein said cylindrical portion housing top comprises an inside surface that is rough.

23. An injection site as claimed in claim 16 wherein the distance between the end of said valve and the outlet is less than 0.5 inches.

24. An injection site for use in an apparatus for administering a parenteral solution to a patient, said injection site comprising:
a housing comprising a unitary molded stopper portion and an arm portion, said stopper portion including a cylindrical portion having an open top and an outlet portion; and
a stopper positioned within said housing, said stopper being accessible through said open top from outside said injection site, said stopper having a substantially flat bottom surface;
said housing arm portion accepting fluids at its input and releasing the fluids from its output across the bottom surface of said stopper to provide a substantially self-priming injection site.

25. An injection site as claimed in claim 24 wherein said arm portion is substantially perpendicular to said stopper portion.

26. An injection site as claimed in claim 24 wherein said arm portion includes a ramp that directs the fluid across the bottom surface of said stopper.

27. An injection site as claimed in claim 26 wherein the input to said arm portion and the outlet portion of said stopper portion are substantially parallel to one another.

* * * * *